United States Patent
Heaton et al.

(10) Patent No.: US 9,625,251 B2
(45) Date of Patent: Apr. 18, 2017

(54) FACIAL MOVEMENT AND EXPRESSION DETECTION AND STIMULATION

(71) Applicants: MASSACHUSETTS EYE & EAR INFIRMARY, Boston, MA (US); The General Hospital Corporation, Boston, MA (US)

(72) Inventors: James Tracey Heaton, Mansfield, MA (US); Theresa A. Hadlock, Arlington, MA (US)

(73) Assignees: Massachusetts Eye & Ear Infirmary, Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/760,944

(22) PCT Filed: Jan. 14, 2014

(86) PCT No.: PCT/US2014/011489
§ 371 (c)(1),
(2) Date: Jul. 14, 2015

(87) PCT Pub. No.: WO2014/110575
PCT Pub. Date: Jul. 17, 2014

(65) Prior Publication Data
US 2015/0354941 A1    Dec. 10, 2015

Related U.S. Application Data

(60) Provisional application No. 61/752,175, filed on Jan. 14, 2013.

(51) Int. Cl.
*A61B 5/00*    (2006.01)
*G01B 11/00*    (2006.01)
(Continued)

(52) U.S. Cl.
CPC ............ *G01B 11/00* (2013.01); *A61B 5/0059* (2013.01); *A61B 5/1103* (2013.01);
(Continued)

(58) Field of Classification Search
CPC ............................ A61B 5/0059; A61B 5/6803
See application file for complete search history.

(56) References Cited

U.S. PATENT DOCUMENTS 4,799,487 A   1/1989 Bleicher
5,410,376 A   4/1995 Cornsweet et al.
(Continued)

FOREIGN PATENT DOCUMENTS

WO    2005/094667    10/2005
WO    2012/073016    6/2012

OTHER PUBLICATIONS

Bracha et al., "Video recording system for the measurement of eyelid movements during classical conditioning of the eyeblink response in the rabbit," Journal of Neuroscience Methods, 30;125(1-2):173-181 (May 2003).
(Continued)

*Primary Examiner* — William Levicky
(74) *Attorney, Agent, or Firm* — Fish & Richardson P.C.

(57) ABSTRACT

The disclosure features systems and methods for detecting a user's facial movement and expression, that include a plurality of radiation sources, a plurality of radiation detectors, where each radiation detector is paired with a different one of the radiation sources and configured to detect radiation emitted by its paired radiation source, and a controller connected to the radiation detectors and configured to receive signals corresponding to measurements of emitted radiation from each of the radiation detectors, determine, for each radiation source-detector pair, information about whether a radiation path between the source and detector is
(Continued)

blocked by a portion of the user's face, and determine a facial movement or expression of the user based on the information.

20 Claims, 8 Drawing Sheets

(51) Int. Cl.
  *A61N 1/04* (2006.01)
  *A61N 1/36* (2006.01)
  *A61B 5/11* (2006.01)
  *A61B 5/16* (2006.01)

(52) U.S. Cl.
  CPC .............. *A61B 5/1126* (2013.01); *A61B 5/16* (2013.01); *A61B 5/6803* (2013.01); *A61N 1/0452* (2013.01); *A61N 1/0456* (2013.01); *A61N 1/0476* (2013.01); *A61N 1/0492* (2013.01); *A61N 1/36014* (2013.01)

(56) References Cited

U.S. PATENT DOCUMENTS

| | | | |
|---|---|---|---|
| 5,823,938 | A | 10/1998 | Hernandez |
| 5,843,147 | A | 12/1998 | Testerman et al. |
| 5,867,587 | A | 2/1999 | Aboutalib et al. |
| 6,407,724 | B2* | 6/2002 | Waldern .............. G02B 5/1885 345/7 |
| 7,071,831 | B2 | 7/2006 | Johns |
| 7,616,125 | B2 | 11/2009 | Johns |
| 7,815,311 | B2 | 10/2010 | Johns et al. |
| 2003/0023297 | A1 | 1/2003 | Byers et al. |
| 2004/0233061 | A1 | 11/2004 | Johns |
| 2006/0202841 | A1 | 9/2006 | Johns |
| 2009/0018419 | A1* | 1/2009 | Torch .................. A61B 3/0066 600/318 |
| 2010/0114240 | A1 | 5/2010 | Guntinas-Lichius et al. |
| 2011/0121976 | A1 | 5/2011 | Johns et al. |
| 2011/0292338 | A1 | 12/2011 | Iwanaga |

OTHER PUBLICATIONS

Chen et al., "Closed loop eyelid reanimation system with real-time blink detection and electrochemical stimulation for facial nerve paralysis," IEEE Int'l Symposium on Circuits and Systems, pp. 549-552 (2009).

Filler, "Regaining Computer use with the Blink of an Eye," Virginia Commonwealth University, 20 pages (May 2, 2008).

Frigerio et al., "A Closed-Loop Stimulation System Supplemented with Motoneurone Dynamic Sensitivity Replicates Natural Eye Blinks," Otolaryngology—Head and Neck Surgery 2012, 146(2):230-233 (Dec. 2012).

Griffin et al., "Potential of an Electric Prosthesis for Dynamic Facial Reanimation," Otolaryngology—Head and Neck Surgery, 145(3):365-368 (Mar. 2011).

Heaton et al., "A system for studying facial nerve function in rats through simultaneous bilateral monitoring of eyelid and whisker movements," Journal of Neuroscience Methods; 30;171(2):197-206 (Jun. 2008).

International Preliminary Report on Patentability in International Application No. PCT/US2014/011489, mailed Jul. 23, 2015, 6 pages.

International Search Report and Written Opinion in International Application No. PCT/US2014/011489, mailed Apr. 24, 2014, 8 pages.

Knipling et al., "Vehicle-Based Drowsy Driver Detection: Current Status and Future Prospects," National Highway Traffic Safety Administration, Office of Crash Avoidance Research, 23 pages (Apr. 1994).

Lee, B.-G., "Driver Alertness Monitoring Using Fusion of Facial Features and Bio-Signals," IEEE Sensors Journal 12(7): 2416-2422 (2012).

Miller et al., "A fiber optic-based system for behavioral eyeblink measurement in a MRI environment," Journal of Neuroscience Methods;141(1):83-87 (Jan. 30, 2005).

Ryan et al., "A long-range, wide field-of-view infrared eyeblink detector," Journal of Neuroscience Methods.;152(1-2):74-82 (Apr. 15, 2006).

Smith et al., "Monitoring Head/Eye Motion for Driver Alertness with One Camera," Proceedings, 15th International Conference on Pattern Recognition, vol. 4, pp. 636-642 (2000).

Thompson et al., "A system for quantitative analysis of associative learning. Part 1. Hardware interfaces with cross-species applications," Journal of Neuroscience Methods; 54(1):109-117 (Sep. 1994).

Unknown Author, "Eye Tracker May Save the Lives of Drowsy Drivers (and Everyone Around Them)," Eye Doctor Guide, publically available before Jan. 14, 2013 [retrieved on Oct. 22, 2015]. Retrieved from the Internet: URL<http://www.eyedoctorguide.com/eye_care/eye_tracking_prevent_sleep_driving.html>, 2 pages.

* cited by examiner

FACIAL MOVEMENT AND EXPRESSION DETECTION AND STIMULATION

CROSS-REFERENCE TO RELATED APPLICATIONS

This application is a national phase application of International Patent Application No. PCT/US2014/011489, filed on Jan. 14, 2014, which claims priority to U.S. Provisional Patent Application No. 61/752,175, filed on Jan. 14, 2013, the entire contents of each of which are incorporated by reference herein.

STATEMENT AS TO FEDERALLY SPONSORED RESEARCH

This invention was made with Government support under National Institute of Neurological Disorders and Stroke Grant # R01-NS070167. The Government has certain rights in the invention.

TECHNICAL FIELD

This disclosure relates to detection and stimulation of facial expressions and facial movements such as eye blinks.

BACKGROUND

Ipsilateral peripheral facial nerve palsy (FNP) due to an impaired facial nerve affects 0.3% of the population per year in Western Europe and the United States. The most common cause is Bell's Palsy, which afflicts about 20 out of every 100,000 individuals yearly, but there are many other causes as well, including traumas, infections, neoplasms, iatrogenic palsies, and congenital palsies. Loss of the blink reflex and eyelid closure with concomitant corneal damage is one of the most severe consequences of FNP.

SUMMARY

This disclosure features systems and methods for detecting and stimulating facial expressions and facial movements such as eye blinks. The systems include or consist of one or more radiation sources and one or more radiation detectors. The sources and detectors are paired so that the radiation emitted by each one of the sources is detected by one of the detectors. The sources and detectors are positioned so that, for each source-detector pair, radiation emitted by the source propagates adjacent to a different portion of the user's face. Depending upon the user's facial expression (i.e., the position of different features of the user's face), radiation emitted from each source may be blocked by the user's face (so that no radiation reaches the corresponding detector), or radiation may remain unblocked, so it is detected by the corresponding detector. By determining which of the radiation sources are blocked by the user's face, the user's facial movements and facial expression can be inferred. The systems can be integrated into a wearable prosthetic device such as eyeglass frames, or implemented as an apparatus that can be attached to a user's existing eyeglasses.

The systems can also include one or more electrodes configured to stimulate impaired facial nerves in one side of the user's face. For example, information about facial movements on one side of a user's face determined from the source-detector pairs can be transmitted to a controller, which can then transmit signals to the one or more electrodes to stimulate complementary facial movements in the other side of the user's face. By doing so, the user's entire face appears to move and respond to stimuli in a concerted, symmetric, and ordinary way, despite the impairment to his or her facial nerves.

In general, in a first aspect, the disclosure features systems for detecting a user's facial movement and expression, wherein the systems include or consist of a plurality of radiation sources, a plurality of radiation detectors, where each radiation detector is paired with a different one of the radiation sources and configured to detect radiation emitted by its paired radiation source, and a controller connected to the radiation detectors and configured to receive signals corresponding to measurements of emitted radiation from each of the radiation detectors, determine, for each radiation source-detector pair, information about whether a radiation path between the source and detector is blocked by a portion of the user's face, and determine a facial movement or expression of the user based on the information.

Embodiments of the systems can include or consist of any one or more of the following features.

The plurality of radiation sources can include at least three or four radiation sources. The system can include a support structure, where the plurality of radiation sources and the plurality of radiation detectors are integrated into or attached to the support structure. The support structure can include eyeglass frames. The plurality of radiation sources and the plurality of radiation detectors can be connected to the controller through or by means of the support structure.

The systems can include a plurality of electrodes each configured to transmit an electrical signal to a facial nerve of the user. The plurality of electrodes can be attached to the support structure. The plurality of electrodes can be connected to the controller through the support structure. The controller can be configured to transmit electrical signals to the plurality of electrodes to apply the electrical signals to one or more facial nerves of the user.

Each of the plurality of radiation sources can emit radiation having a different central wavelength. Radiation emitted by each of the radiation sources can have a modulation frequency and a modulation phase, and the modulation phase of the emitted radiation can be different for each of the radiation sources. Each of the radiation detectors can include a photodiode.

The controller can be configured to determine the user's facial movement or expression based on a rate of change of detected emitted radiation from one or more of the plurality of radiation sources. The controller can be configured to determine whether the user's facial movement or expression corresponds to one of at least eight different facial movements or expressions. The at least eight different facial movements or expressions can include a forward gaze, a lateral gaze, a downward gaze, an upward gaze, an eye blink, a squeezed eye closure, a smile, and an eyebrow raised movement or expression.

The support structure can include a member to which the plurality of radiation sources and the plurality of detectors are attached, and the support structure can be configured to be attached to eyeglass frames.

Embodiments of the systems can also include any of the other features or aspects disclosed herein, in any combination or subcombination, as appropriate.

In another aspect, the disclosure features methods for detecting a user's facial movement or expression, the methods include or consist of: positioning a plurality of pairs of radiation sources and radiation detectors adjacent to a user's face, where each source-detector pair forms a radiation path; for each source-detector pair, directing radiation from the source toward the detector along the radiation path, and determining information about whether the radiation path is blocked by a portion of the user's face; and determining a facial movement or expression of the user based on the information.

Embodiments of the methods can include or consist of any one or more of the following features.

The radiation can include infrared radiation. Each of the radiation sources can emit radiation having a different central wavelength. The method can include modulating the radiation emitted by each of the radiation sources according to a modulation frequency and a modulation phase, where the modulation phases of each of the radiation sources are different.

The methods can include transmitting signals corresponding to measurements of emitted radiation from the radiation detectors to a controller through a support structure. The support structure can include eyeglass frames.

The methods can include transmitting electrical signals to a plurality of electrodes positioned on the user's face based on the facial movement or expression of the user. The method can include selecting at least one of an amplitude and a number of pulses of the transmitted electrical signals to cause movement of a portion of the user's face based on the facial movement or expression of the user.

The methods can include determining the user's facial movement or expression based on a rate of change of detected radiation emitted from one or more of the plurality of radiation sources. The methods can include determining whether the user's facial movement or expression corresponds to one of at least eight different facial movements or expressions. The at least eight different facial movements or expressions can include a forward gaze, a lateral gaze, a downward gaze, an upward gaze, an eye blink, a squeezed eye closure, a smile, and an eyebrow raised movement or expression. The methods can include assessing a level of alertness of the user based on the facial movement or expression.

Embodiments of the methods can also include any of the other features or steps disclosed herein, in any combination, as appropriate.

In general, although specific embodiments are disclosed herein, combinations and sub-combinations of features disclosed in connection with different embodiments can be present in other embodiments, which are also within the scope of the disclosure. Unless specifically excluded herein, different combinations of features are operable and can be used together. The features, aspects, and steps disclosed herein—although they may be discussed in the context of specific embodiments for illustrative purposes—are not restricted to the embodiments in which they are disclosed, but instead are general to this disclosure and to the various embodiments disclosed herein and appreciated by a person of ordinary skill in the art. In the claims, the phrase "comprising," which is open-ended and means "includes, but is not limited to," can be replaced by the phrase "consisting of," which is closed and means "includes only."

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

General Considerations

The effects of FNP are both physiological and social. For example, loss of the blink reflex due to impaired facial nerves can lead to eye irritation and even permanent corneal damage, as the eye is not properly lubricated and particulate matter can come into contact with the ocular surface. Further, for a subject afflicted with FNP, the subject's asymmetrical facial response (e.g., blinking with only a single eye, smiling and/or raising eyebrows on only one side of his or her face) to a variety of stimuli can be a source of embarrassment and self-consciousness. Fortunately, however, in many cases the subject's facial nerves remain largely intact and capable of eliciting a variety of facial movements when suitably stimulated. Accordingly, where one half of the subject's face responds normally by adopting a particular facial expression, the other half of the subject's face can, in principle, be stimulated to produce a complementary response (i.e., the same facial expression), giving the subject's entire face the appearance of moving concertedly to adopt the same facial expression on both sides of the face.

To stimulate half of the subject's face to produce a facial expression that mimics the other half of the subject's face, the subject's facial expression in the healthy other half of his or her face must first be determined. The present disclosure features systems and methods for determining facial expressions of a user (i.e., a wearer) of the systems. In particular, the systems and methods establish radiation paths between pairs of radiation sources and detectors that are positioned adjacent to various portions of the subject's face. By determining which of the radiation paths are blocked and which are unblocked by portions or parts of the subject's face, the systems and methods can determine the subject's facial expression. This information can then be used to stimulate one or more electrodes to induce a complementary response (i.e., produce a similar facial expression) in the other half of the subject's face.

Systems and Methods for Detecting Facial Expressions

Figure 1:
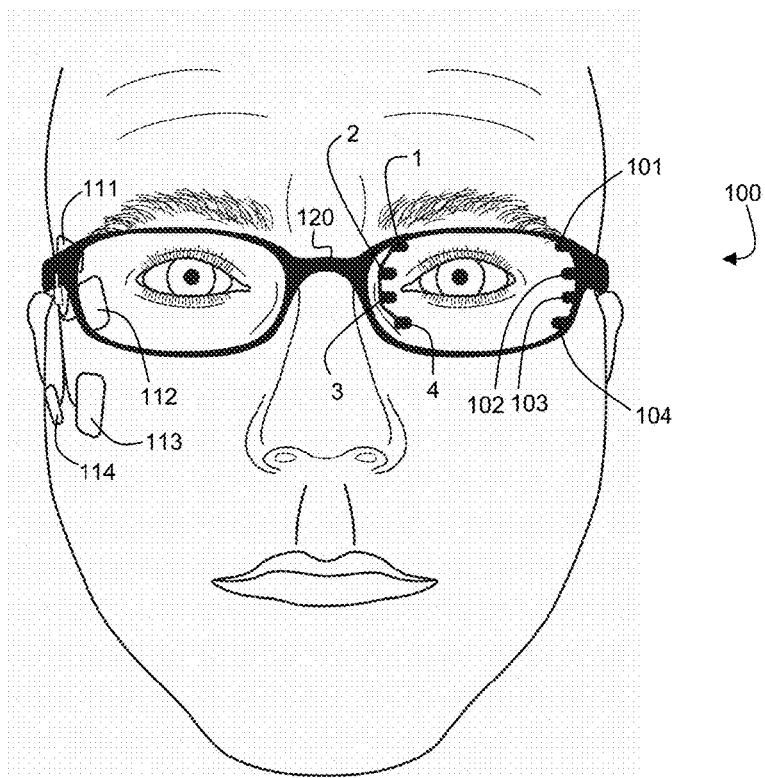
FIG. 1 is a schematic diagram of a front view of a facial movement detection system.

FIG. 1 is a schematic diagram of one example of a system 100 for detecting a user's facial expression. System 100 includes radiation, e.g., visible or infrared light, sources 1-4, e.g., LEDs or lasers, and detectors 101-104. Radiation sources 1-4 and 100-104 are paired so that source 1 generates radiation that is detected only by detector 101, source 2 generates radiation that is detected only by detector 102, source 3 generates radiation that is detected by detector 103, and source 4 generates radiation that is detected only by detector 104. Each of the sources and detectors is positioned at a specific different location adjacent to the face of the subject so that each source-detector pair establishes a radiation path that extends from the source to the detector. In different implementations, the system can include one, two, three, four, or more pairs of radiation sources and detectors. During operation of system 100, each source emits radiation. If the radiation path between the source and its paired detector is unblocked by the user's face, then the paired detector measures the emitted radiation from the source. However, if the radiation path between the source and its paired detector is partially or fully blocked by a portion of the user's face, then the paired detector measures a reduced signal (or no signal) due to the emitted radiation from the source. As will be explained subsequently, the pattern of blocked and unblocked radiation paths between the source-detector pairs can be used to infer the user's facial expression.

In FIG. 1, radiation sources 1-4 and detectors 101-104 are positioned proximate to the user's eye on a side of the user's face that is not affected by FNP. In other words, information about the blocked and unblocked radiation paths between sources 1-4 and detectors 101-104 can be used to stimulate nerves in the other side of the user's face (e.g., the side in FIG. 1 where no sources or detectors are positioned) to produce a complementary response in the other side. In some embodiments, system 100 includes a plurality of electrodes 111-114 attached to different regions of the side of the user's face afflicted with FNP. These electrodes will be discussed further subsequently.

In some embodiments, system 100 includes a support structure 120. As shown in FIG. 1, the support structure can have a variety of forms. For example, support structure 120 can be implemented as eyeglass frames, where radiation sources 1-4 and detectors 101-104 are integrated into, or attached to, the support structure. More generally, support structure 120 can be implemented as any structure that can be worn by the user and that maintains sources 1-4 and detectors 101-104, or any other number of source-detector pairs, in position relative to one another so that radiation paths are reliably established between the pairs of sources and detectors when support structure 120 is worn by the user. Other examples of suitable support structures include goggles, helmets, visors, and specific hats, which can also be used with any number of source-detector pairs.

In different embodiments, support structure 120 can take different forms. For example, referring to FIG. 2, support structure 120 can be implemented as a support member to which sources 1-4 and detectors 101-104 are attached. In some embodiments, support structure 120 can be affixed directly to the face of the user with, e.g., tape, or a deposited adhesive medium. In certain embodiments, the support member can be configured to attach to an apparatus such as conventional eyeglass frames worn by the user. For example, the support member can include an attachment mechanism such as a clip, a magnetic connector, and/or a threaded connector so that the support member can be fixed, e.g., rigidly fixed, to the eyeglass frames. Other examples of apparatus to which support structure 120 can be attached include goggles, helmets, visors, and specific hats.

Figure 17:
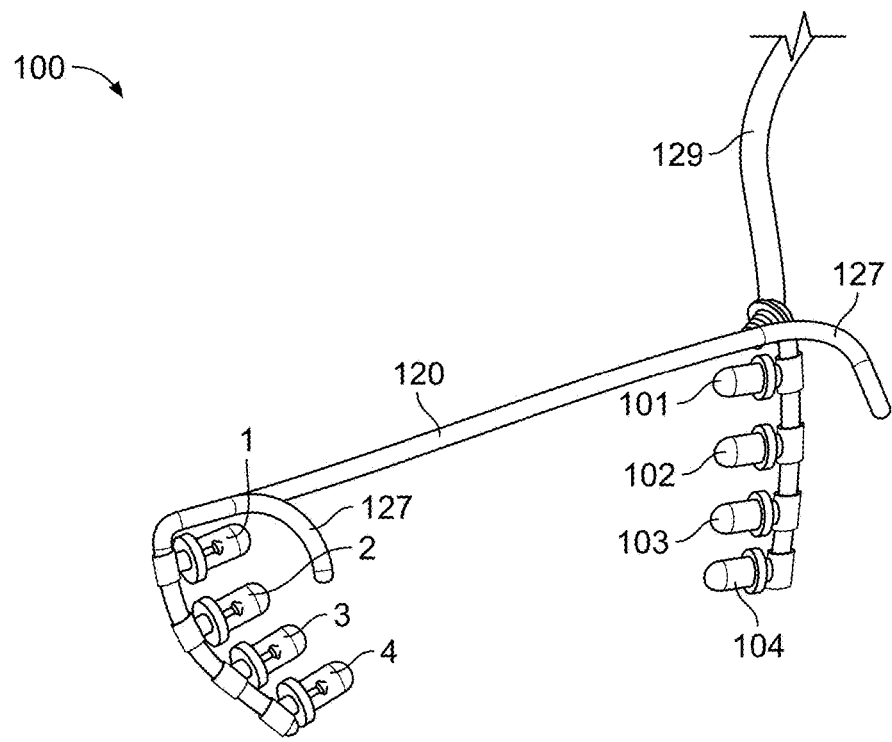
FIGS. 17-21 are photographs of an embodiment of a facial movement detection system that includes an attachment mechanism to connect to goggles and eyeglass frames.
Figure 18:
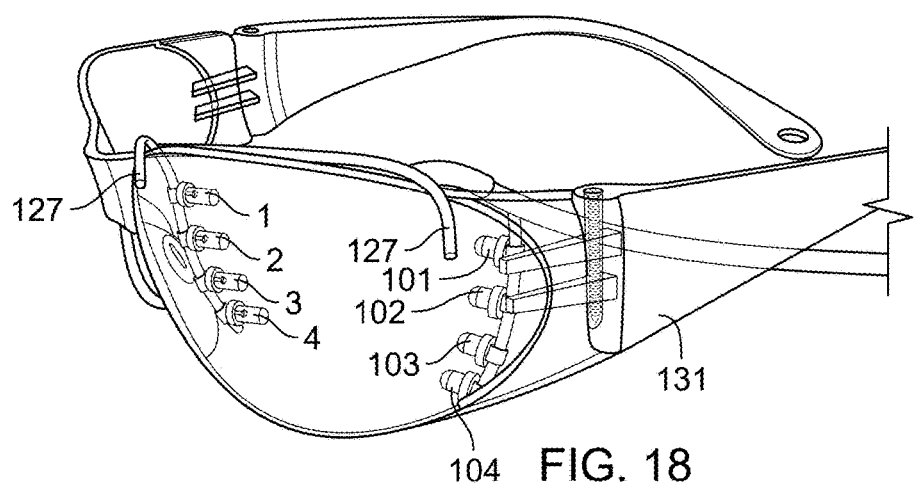
Figure 19:
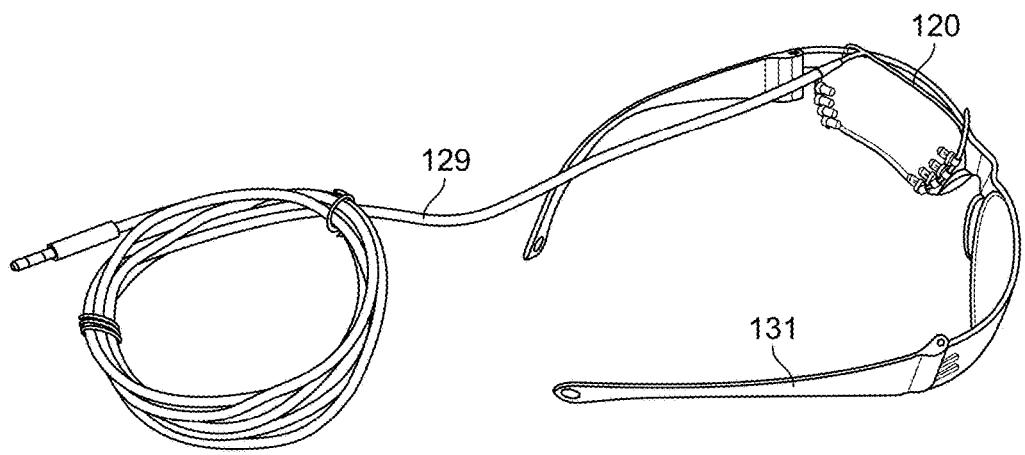

FIGS. 17-19 are photographs of an embodiment of system 100 that includes a support structure 120 to which sources 1-4 and detectors 101-104 are attached. Support structure 120 includes an attachment mechanism 127 in the form of a flexible wire or clip that allows system 100 to be attached to goggles 131. As shown in FIG. 18, attachment mechanism 127 is wrapped around a portion of goggles 131 to affix system 100 to the goggles. In embodiments where system 100 is configured to attach to a separate apparatus (e.g., goggles or eyeglass frames), the apparatus may not include internal conductors within the apparatus that permit sources 1-4 and detectors 101-104 to connect to a controller. Instead, as shown in FIGS. 17-19, system 100 can include a cable 129 that connects to the controller to enable the controller to transmit signals to, and receive signals from, sources 1-4 and detectors 101-104.

Figure 20:
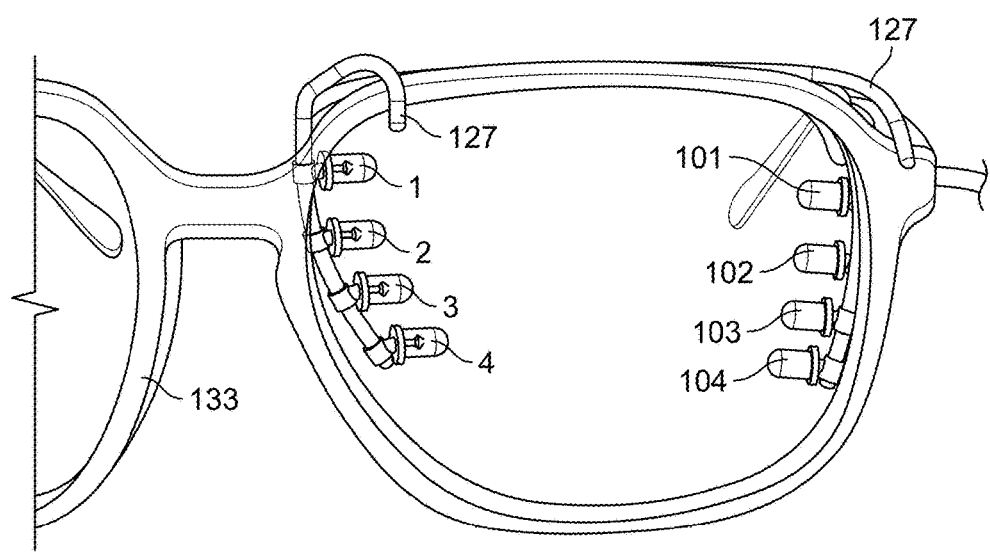
Figure 21:
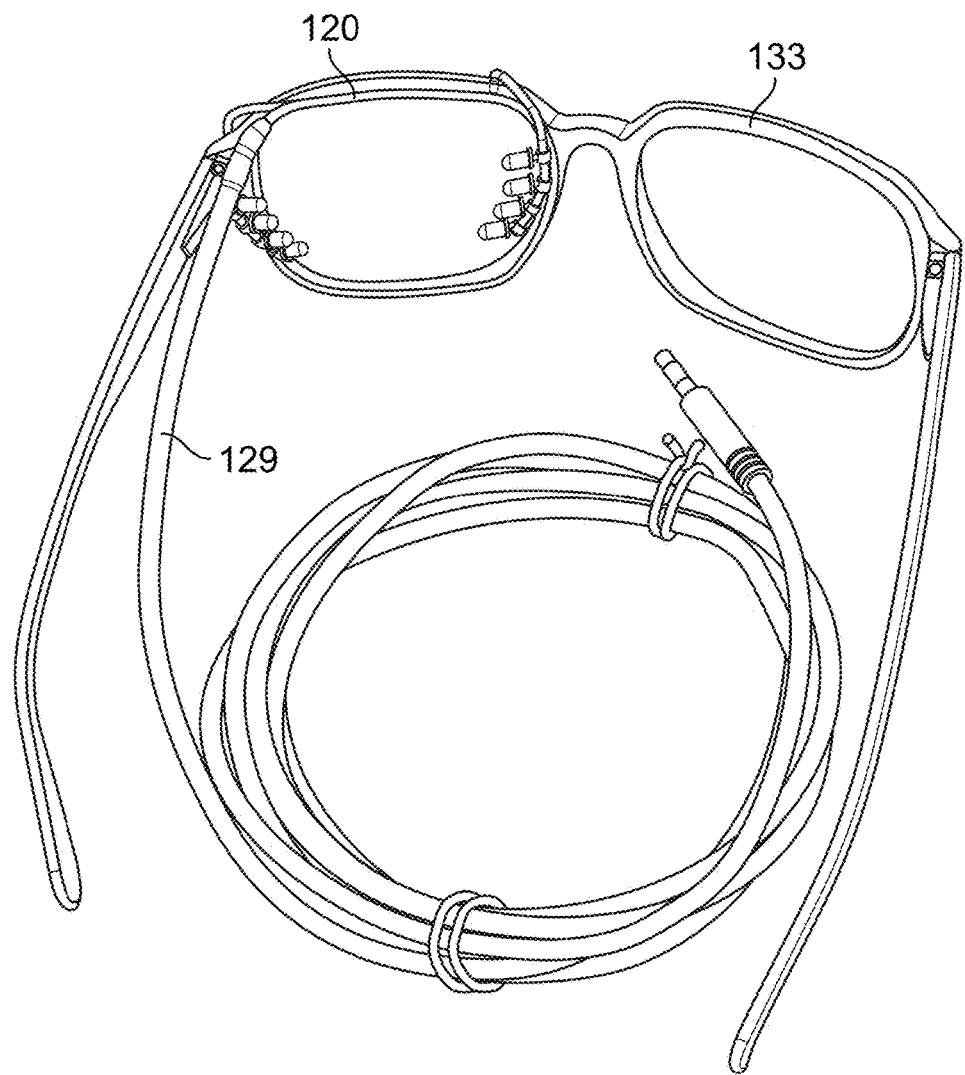

FIGS. 20-21 show the same embodiment of system 100 as in FIGS. 17-19, connected to eyeglass frames 133. The attachment mechanism is wrapped around a portion of eyeglass frames 133 to secure system 100 to the frames.

A variety of devices can be used as sources 1-4 to emit radiation. In some embodiments, for example, sources 1-4 can be light emitting diodes (e.g., QEC123 LEDs, with a central emission wavelength of 880 nm, available from Fairchild Semiconductor, San Jose, Calif.). Sources 1-4 can generally emit radiation in the ultraviolet, visible, and/or infrared regions of the electromagnetic spectrum. However, human eyes are relatively insensitive to radiation in the infrared region of the spectrum. Accordingly, in certain embodiments, each of sources 1-4 emits radiation in the infrared region, ensuring that the user of system 100 is not cognizant of the emission from sources 1-4. Another advantage of infrared radiation is that it is not typically strongly absorbed by ocular tissues. As a result, infrared emission from sources 1-4 is less likely to cause eye damage than emitted radiation of comparable intensity in the visible and/or ultraviolet regions of the spectrum.

A variety of devices can be used as detectors 101-104 to detect the emitted radiation. In some embodiments, for example, detectors 101-104 can be photodiodes (e.g., QSC114 silicon infrared photodiodes with a peak sensitivity of 880 nm, available from Fairchild Semiconductor, San Jose, Calif.). Detectors 101-104 are generally selected so that they efficiently detect radiation in the wavelength range emitted by sources 1-4.

As disclosed above, sources 1-4 and detectors 101-104 are paired and/or oriented so that radiation emitted by each one of the sources is detected by only one of the detectors. The sources and detectors can be paired in a variety of ways. In certain embodiments, each of sources 1-4 emits radiation having a different central wavelength (where the central wavelength is the wavelength at the center of a source's emission band), and each of detectors 101-104 is configured to detect radiation at only one of the four emission wavelengths. In this manner, each detector selectively detects emission from only one source. The radiation from each source, although corresponding to different central wavelengths, can be in the same general region of the electromagnetic spectrum (e.g., the infrared region), or emitted radiation from some of the sources can be in one or more regions (e.g., the visual region and/or the ultraviolet region) that are different from the emitted radiation from other sources (e.g., the infrared region).

Figure 11:
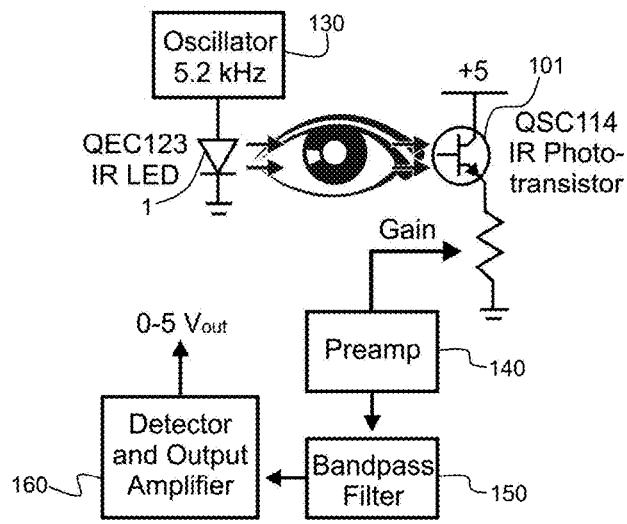
FIG. 11 is a schematic diagram showing a source-detector pair for detecting facial movements.

In some embodiments, sources 1-4 and detectors 101-104 can be paired according to a modulation phase applied to the emitted radiation from the sources. FIG. 11 shows a schematic diagram of a detection circuit for source 1 and detector 101. Each of sources 1-4 and detectors 101-104 can include a similar detection circuit, and certain components of the detection circuit shown in FIG. 11 can be shared among the detection circuits of multiple sources and detectors.

In FIG. 11, source 1 (a light emitting diode) emits radiation in the infrared region of the spectrum. An oscillator 130 applies a variable driving voltage to source 1 to generate the emitted radiation. For example, the driving voltage can have a frequency of 5.2 kHz and a particular phase value. In general, both the frequency and phase value of the driving voltage can be selected as desired. For example, the driving voltage can have a frequency greater than 100 Hz (e.g., greater than 200 Hz, greater than 500 Hz, greater than 1 kHz, greater than 5 kHz, greater than 10 kHz, greater than 100 kHz, greater than 200 kHz, greater than 500 kHz) and/or less than 500 MHz (e.g., less than 200 MHz, less than 100 MHz, less than 50 MHz, less than 10 MHz, less than 1 MHz). As another example, the phase value can be 0° or more (e.g., 30° or more, 60° or more, 90° or more, 180° or more, 270° or more, 330° or more).

When the driving voltage is applied to source 1, source 1 emits radiation that is modulated according to the same (or similar) frequency and/or phase of the driving voltage. Accordingly, the range of frequencies and phases discussed above for the driving voltage apply also to the modulation frequency and phase of the emitted radiation.

Detector 101 measures the radiation emitted by source 1, and can also measure radiation emitted by the other sources (e.g., sources 2-4) in system 100. A preamplifier 140 amplifies the signal generated by detector 101 in response to the emitted radiation. The amplified signal is then filtered by bandpass filter 150 to isolate the portion of the signal corresponding to the radiation emitted by source 1 (and also to reject ambient light measured by detector 101). This portion of the signal is then amplified by amplifier 160 (e.g., Arduino Mini Pro, available from Arduino, Santa Fe, Argentina).

To achieve pairing between source 1 and detector 101 (e.g., to isolate the portion of the signal corresponding to radiation emitted by source 1), in some embodiments the modulation phases of the emitted radiation from each of sources 1-4 are different. Bandpass filter 150 can then isolate the portion of the signal corresponding to radiation emitted by source 1 by filtering out signal components with modulation phases that differ from the modulation phase of source 1.

In certain embodiments, to achieve pairing between source 1 and detector 101, the modulation frequencies of the emitted radiation from each of sources 1-4 are different. Bandpass filter 150 can then isolate the portion of the signal corresponding to radiation emitted by source 1 by filtering out signal components with modulation frequencies that differ from the modulation frequency of source 1.

In some embodiments, a combination of any two or more (or even all three) methods for pairing (e.g., different emission wavelengths, modulation frequencies, and/or modulation phases) can be used. Each of sources 1-4 is paired with one of detectors 101-104 so that emission from each one of the sources is detected by substantially only one of the detectors.

Figure 2:
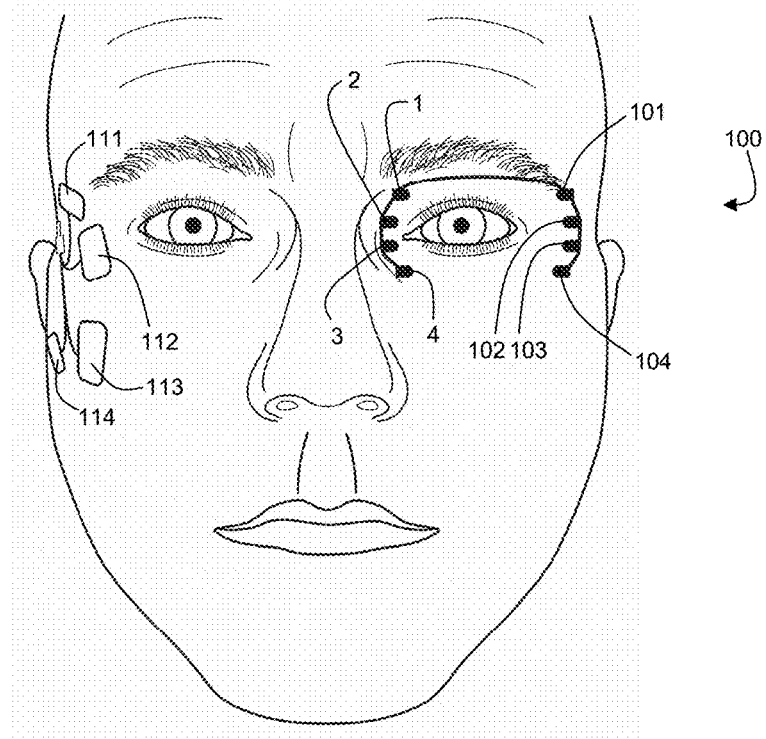
FIG. 2 is a schematic diagram showing a plurality of radiation sources and detectors for detecting facial movements.

Although system 100 includes four source-detector pairs in FIGS. 1 and 2, more generally, system 100 can include any number of source-detector pairs. In general, by using more source-detector pairs, movements of a larger number of different regions of the user's face can be detected, which can increase the number of facial expressions that can be distinguished and/or increase the likelihood that a particular detected facial expression is correct. In certain embodiments, for example, the number of source-detector pairs can be 2 or more (e.g., 3 or more, 4 or more, 5 or more, 6 or more, 8 or more, 10 or more, 15 or more, or even more).

When the radiation path between a particular source and its paired detector (e.g., the straight-line path between the source and the detector) is not blocked by any portion of the user's face, radiation emitted by the source is detected by the paired detector, and the detector generates a relatively strong voltage signal that is related to the intensity of the detected radiation. However, when the radiation path between the source and its paired detector is partially or completely blocked by a portion of the user's face, some or all of the emitted radiation from the source is scattered. As a result, the paired detector generates a comparatively weaker (or zero) voltage signal that reflects the reduced intensity of the detected radiation, relative to the situation when the radiation path is unblocked. Thus, the signals generated by each of detectors 101-104 provide direct information about which of the radiation paths defined by the source-detector pairs are unblocked, and which are (partially or fully) blocked. Typically, the signals generated by detectors 101-104 are assigned a binary value (e.g., 1=unblocked, 0=partially or fully blocked).

As shown in FIGS. 1 and 2, the radiation sources and detectors are positioned relative to the user's face so that information about which radiation paths are blocked, combined with information about the positions of the sources and detectors, can be used to infer the facial expression of the user. In general, the positions of the sources and detectors can be selected as desired to provide information about different portions of the user's face. FIGS. 1 and 2 show an embodiment of system 100 in which source 1 and detector 101 are positioned to define a radiation path adjacent to the user's supraorbital fat pad, source 2 and detector 102 are positioned to define a radiation path adjacent to the center of the user's cornea, source 3 and detector 103 are positioned to define a radiation path adjacent to the user's lower eyelid, and source 4 and detector 104 are positioned to define a radiation path adjacent to the user's malar fat pad. On the basis of the four binary signals (disclosed above) corresponding to each of the radiation paths between the source-detector pairs, different facial expressions of the user can be distinguished.

Figures 3, 4, 5, 6:
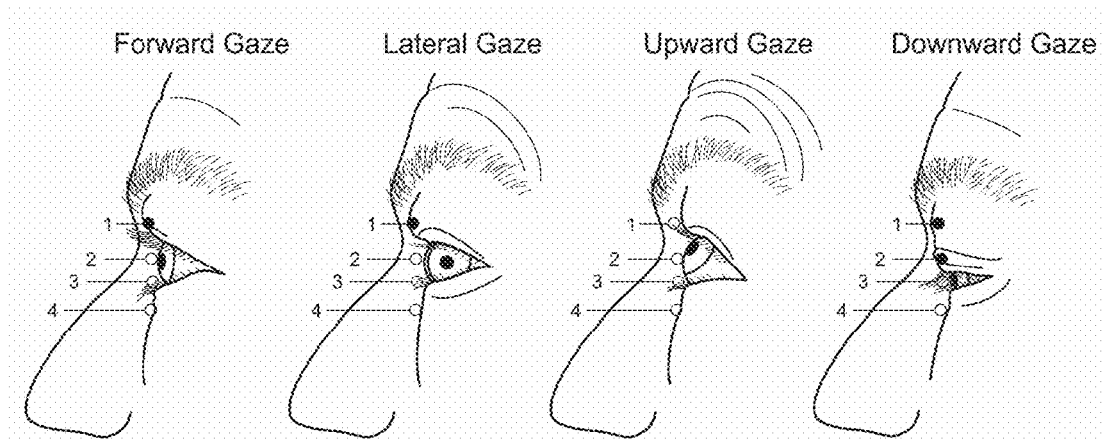
FIG. 3 is a schematic diagram showing a plurality of radiation sources for detecting a forward gaze.
FIG. 4 is a schematic diagram showing a plurality of radiation sources for detecting a lateral gaze.
FIG. 5 is a schematic diagram showing a plurality of radiation sources for detecting an upward gaze.
FIG. 6 is a schematic diagram showing a plurality of radiation sources for detecting a downward gaze.

FIGS. 3-10 show examples of different facial expressions that can be adopted by the user, and the effect of the facial expressions on the radiation paths between the source-detector pairs. In FIG. 3, the user's facial expression is a forward gaze. The radiation path between source 1 and detector 101 is blocked by the supraorbital fat pad, but the radiation paths between sources 2-4 and detectors 102-104 are unblocked. Thus, measured signals from detectors 101-104 which yield a binary sequence of 0-1-1-1 (corresponding to the radiation paths, in order, between source 1 and detector 101, between source 2 and detector 102, between source 3 and detector 103, and between source 4 and detector 104) indicate that the user's facial expression may correspond to a forward gaze.

In FIG. 4, the user's facial expression is a lateral gaze (e.g., no change in the positions of the lower eyelid, or supraorbital or malar fat pads relative to FIG. 3, only a change in the direction of the user's eye). Measured signals from detectors 101-104 therefore yield a binary sequence of 0-1-1-1, the same sequence as in FIG. 3. Thus, for example, if the user's facial expression changes from a forward gaze to a lateral gaze or vice versa; system 100 will not stimulate any of the user's facial nerves, since this change in expression does not substantially change the orientations of the different portions of the user's face.

In FIG. 5, the user's facial expression is an upward gaze. Relative to FIG. 3, the user's supraorbital fat pad is withdrawn, so that all radiation paths are unblocked. Measured signals from detectors 101-104 yield a binary sequence of 1-1-1-1, indicating that his or her facial expression may correspond to an upward gaze.

Figures 7, 8, 9, 10:
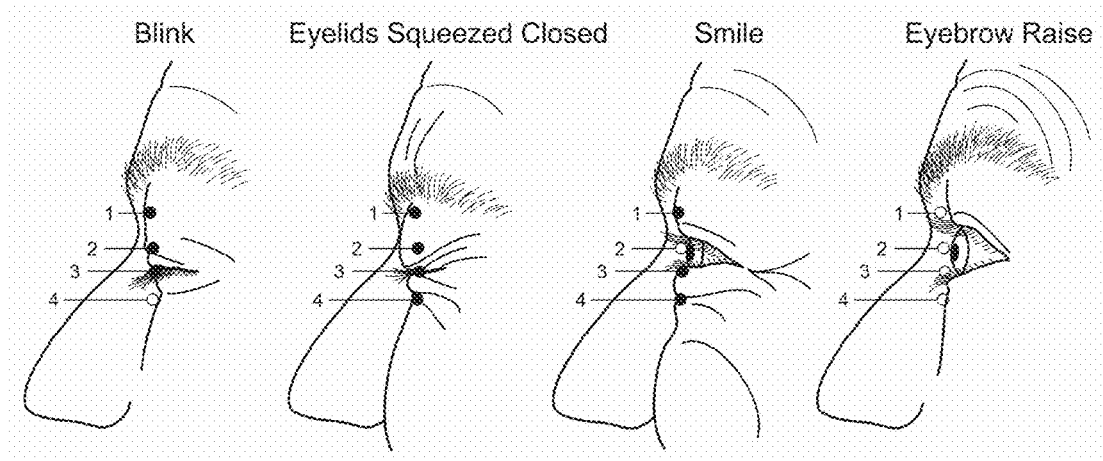
FIG. 7 is a schematic diagram showing a plurality of radiation sources for detecting an eye blink.
FIG. 8 is a schematic diagram showing a plurality of radiation sources for detecting eyelids squeezed closed.
FIG. 9 is a schematic diagram showing a plurality of radiation sources for detecting a smile.
FIG. 10 is a schematic diagram showing a plurality of radiation sources for detecting an eyebrow raise.

In FIG. 10, the user's facial expression is an eyebrow raise. All radiation paths are unblocked, and measured signals from detectors 101-104 yield a binary sequence of 1-1-1-1, which is the same as the sequence for the upward gaze expression in FIG. 5. Comparing FIGS. 5 and 10, however, the orientation of different portions of the user's face in each expression is similar—it is primarily only the direction of the user's eye that differs. Thus, for example, if the user's facial expression changes from an upward gaze to an eyebrow raise or vice versa, system 100 will not change the ongoing pattern of facial nerve stimulation, since this change in expression does not substantially change the orientations of the different portions of the user's face.

In FIG. 6, the user's facial expression is a downward gaze. Relative to FIG. 3, the user's upper eyelid is lowered so that the radiation paths between source 1 and detector 101, and between source 2 and detector 102, are blocked. Measured signals from detectors 101-104 yield a binary sequence of 0-0-1-1, which is indicative of a downward gaze.

In FIG. 7, the user's facial expression (or facial movement) corresponds to an eye blink. Relative to FIG. 6, movement of the user's upper eyelid and eyelashes at least partially block the radiation path between source 3 and detector 103. Accordingly, measured signals from detectors 101-104 yield a binary sequence of 0-0-0-1, which is distinguishable from the downward gaze facial expression of FIG. 6.

In FIG. 8, the user's facial expression corresponds to eyelids that are squeezed closed. The squeezing of the eyelids and motion of both the supraorbital and malar fat pads blocks each of the radiation pathways, so that measured signals from detectors 101-104 yield a binary sequence of 0-0-0-0, which is characteristic for this facial expression.

In FIG. 9, the user's facial expression corresponds to a smile. Relative to FIG. 3, the user's lower eyelid and malar fat pad have risen, so that the radiation paths between source 3 and detector 103, and between source 4 and detector 104, are now blocked. Measured signals from detectors 101-104 yield a binary sequence of 0-1-0-0, which is indicative of a smile.

In some embodiments, additional information beyond a mere binary sequence corresponding to the measured signals from detectors 101-104 can be used to determine the user's facial expression. For example, referring to FIG. 7, during a blink, the user's upper eyelid and/or eyelashes at least partially blocks the radiation path between source 3 and detector 103. However, depending upon the extent of the downward gaze in FIG. 6, it is also possible that the user's upper eyelid and/or eyelashes will at least partially block the radiation path between source 3 and detector 103. Thus, it is conceivable in some circumstances that both a downward gaze and an eye blink will generate the same binary sequence, 0-0-0-1.

Figure 12:
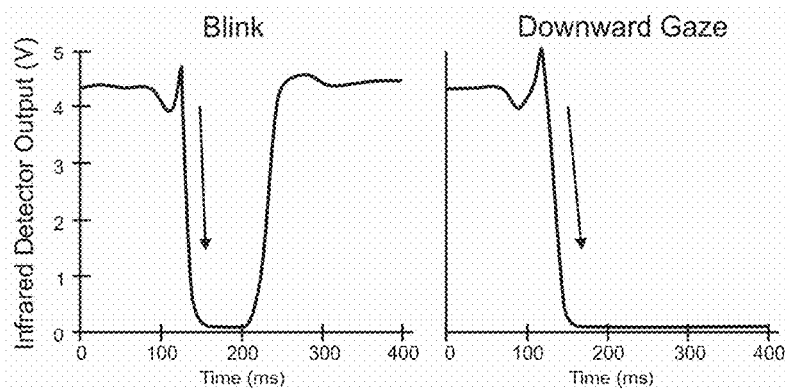
FIG. 12 is a series of graphs showing changes in measured radiation source signals for detecting an eye blink and a downward gaze.
Figure 12:
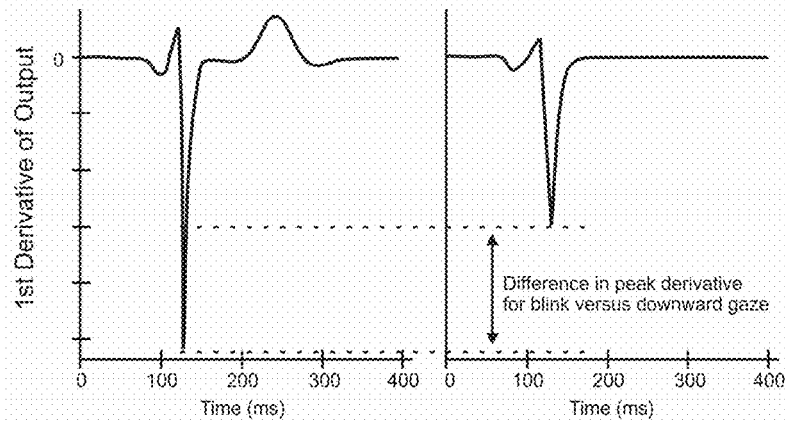

To distinguish between stimulating an eye blink and stimulating a downward gaze in the user, additional information derived from the signals generated by detectors 101-104 can be used. The left upper and right upper panels of FIG. 12 show the output voltage signals from detector 103 for an eye blink (left upper) and a downward gaze (right upper). The signal corresponding to the eye blink decreases in amplitude sharply as the upper eyelid and/or eyelashes block the radiation path between source 3 and detector 103, and then returns to approximately its original amplitude as the user's upper eyelid is withdrawn when the blink is complete. In contrast, the signal corresponding to the downward gaze decreases sharply in amplitude as the user's upper eyelid and/or eyelashes block the radiation path between source 3 and detector 103, and the signal remains at low amplitude as the user's downward gaze is maintained.

This information can then be used to stimulate an appropriate response in the side of the user's face. For example, when the binary sequence 0-0-0-1 is generated, system 100 can be configured to stimulate a blink response in the side of the user's face that suffers from FNP. After stimulating a single blink, if the signal measured by detector 103 remains low (i.e., indicating that the radiation path between source 3 and detector 103 remains blocked), then system 100 can determine that the user's facial movement corresponded not to a blink, but to a downward gaze shift. System 100 can then suspend additional blink stimulation to the user's face as long as the signal measured by detector 103 remains low, which indicates that the user's downward gaze is maintained. When the signal measured by detector 103 returns to a high value (indicating that the radiation path between source 3 and detector 103 is no longer blocked), system 100 once again monitors each of the radiation pathways to detect, among other facial movements and/or expressions, a further blink or downward gaze shift of the user's eye.

In certain embodiments, facial expressions can be distinguished based on the rate of change (e.g., the first derivative) of the signals measured by one or more detectors. The lower left and right hand panels in FIG. 12 show the first derivatives of the measured signals in the upper left and right hand panels respectively. The amplitude of the first derivative of the signal corresponding to the eye blink is significantly larger than the amplitude of the first derivative of the signal corresponding to the downward gaze, due to the faster rate at which the user's eyelid and/or eyelashes move during an eye blink. Thus, the eye blink and the downward gaze can be distinguished based on the differences in their first derivative signal amplitude. For example, system 100 can include a defined threshold value (e.g., selected or hard-coded into system 100, or set by the user) that is used to distinguish between an eye blink and a downward gaze based on the amplitude of the first derivative signal (e.g., the rate of change of the signal generated by detector 103).

Figure 13:
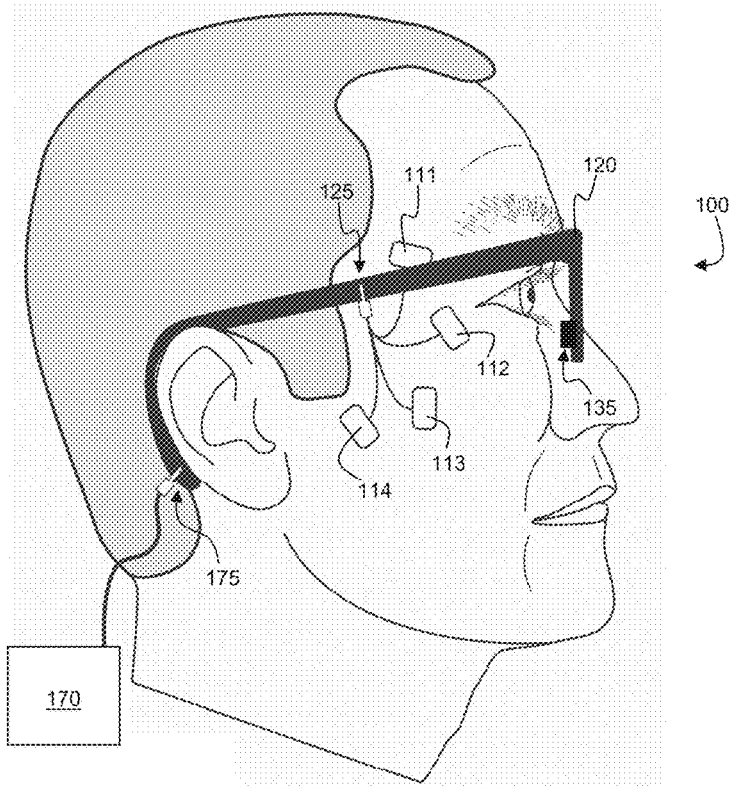
FIG. 13 is a schematic diagram of a side view of a facial movement detection system.

FIG. 13 shows a lateral view of system 100, including a support structure 120 implemented as eyeglass frames. Each of sources 1-4 and detectors 101-104 (not shown in FIG. 13) is electrically connected to an internal conductor bundle that runs through support structure 120. The conductor bundle is connected to port 175. System 100 includes a controller 170 that also connects to port 175. When connected, controller 170 can transmit signals to, and receive signals from, sources 1-4 and detectors 101-104. In some embodiments, as shown in FIGS. 17-21, controller 170 can connect directly to system 100 through cable 129, which is attached to support structure 120 and connected to sources 1-4 and detectors 101-104. In certain embodiments, controller 170 is directly connected to source 1-4 and detectors 101-104, e.g., when controller 170 is directly integrated into support structure 120.

For example, in general, oscillator 130, preamplifier 140, bandpass filter 150, and amplifier 160 are positioned within controller 170. In some embodiments, controller 170 can transmit voltage signals to each of sources 1-4 to cause the sources to emit radiation. The voltage signals can be modulated in frequency and/or in phase, as discussed above in connection with FIG. 11. Controller 170 can also receive signals generated by detectors 101-104, and can amplify the signals using preamplifier 140, filter the signals using bandpass filter 150, and further amplify the signals using amplifier 160.

Based on the signals received from detectors 101-104, controller 170 can also determine the user's facial expression according to the methods described above. In particular, controller can determine a binary sequence based on the signals, and can determine the facial expression based on the binary sequence. In certain embodiments, controller 170 can also use information such as measured signal amplitudes and rates of change of signal amplitudes to determine the user's facial expression.

Systems and Methods of Stimulating Facial Expressions

As disclosed above in connection with FIGS. 1 and 2, in some embodiments, system 100 includes a plurality of electrodes 111-114. The electrodes are electrically connected to a port 125 in support structure 120. When connected, electrodes 111-114 can receive electrical voltage signals from controller 170 to stimulate particular facial nerves of the user.

Although system 100 is shown with four electrodes 111-114, system 100 can generally include any number of electrodes (e.g., 1 or more, 2 or more, 3 or more, 4 or more, 5 or more, 6 or more, 8 or more, or 10 or more). Typically, as more electrodes are used, nerves in the user's face can be stimulated in a more selective fashion. The electrodes can be attached to the user's face using a clinical, electrically conductive adhesive or tape, for example. Alternatively, in certain embodiments, the electrodes can be mounted on a support member attached to structure 120. The support member can be configured to reliably position the electrodes in contact with the user's face at suitable locations for stimulating facial nerves, without the use of adhesives.

Figure 14:
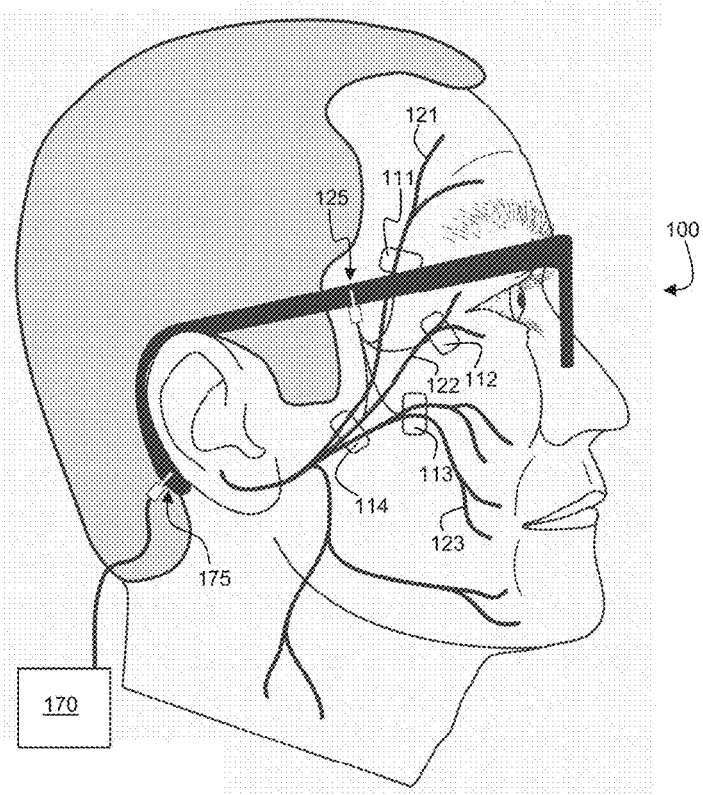
FIG. 14 is a schematic diagram of a side view of a user's facial nerves and the facial movement detection system of FIG. 13.

A variety of different arrangements of electrodes can be used. FIG. 14 shows an embodiment of system 100 in which electrodes 111-114 are positioned in a particular arrangement in which electrode 111 (e.g., the temporal electrode) stimulates the temporal branch 121, electrode 112 (e.g., the zygomatic electrode) stimulates the zygomatic branch 122, and electrode 113 (e.g., the buccal electrode) stimulates the buccal branch 123. Electrode 114, positioned near the junction of the temporal, zygomatic, and buccal branches, functions as the common anode electrode.

Figure 15:
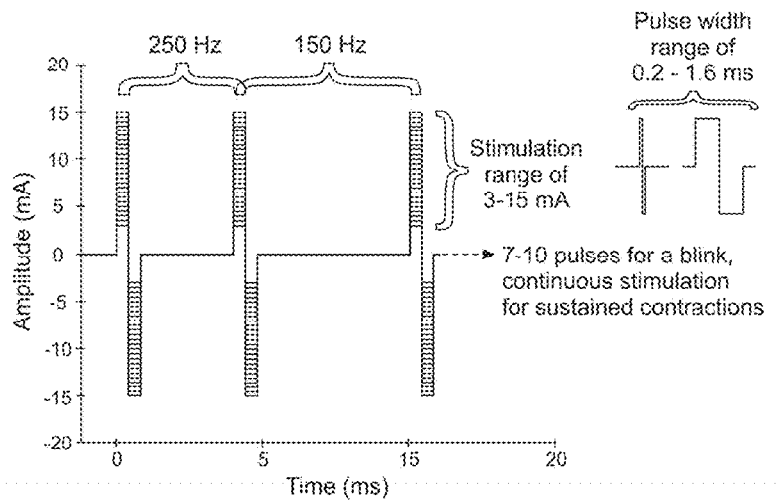
FIG. 15 is a schematic diagram of an electrical waveform for stimulating facial nerves.

In general, controller 170 determines, based on the facial expression on one side of the user's face, an appropriate set of electrical voltage signals to transmit to electrodes 111-114 to stimulate the facial nerves on the other side of his or her face to induce the same (or a similar) facial expression. Typically, the appropriate signals vary depending upon the type of facial expression to be elicited. For example, stimulation pulse trains for eliciting blinks typically include a relatively short series of 7-10 charge-balanced, square-wave pulses, with the first two pulses having a frequency of approximately 250 Hz (4 ms inter-pulse interval), and the remaining pulses having a frequency of approximately 150 Hz (6.6 ms inter-pulse interval), lasting for about 37.3-57.3 s. FIG. 15 shows one example of a pulse train suitable for stimulating eye blinks in a user. The pulse train in FIG. 15 is known to be effective to elicit naturalistic blink kinematics from face surface stimulation similar to that used by the present system. In general, the widths of the pulses in the pulse train can vary from 0.2 ms to 1.6 ms. To elicit other facial movements (e.g., other than eye blinks), pulse trains are typically continuously delivered for the duration of the desired movement or expression, with an amplitude proportional to an extent of facial movement desired.

In some embodiments, there can be a trade-off between pulse width and sensory stimulation, such that longer square pulses elicit blinks or other facial movements at lower stimulus amplitudes, but also generate a stronger sensory response which may be uncomfortable for a user. Stimulation amplitudes for achieving blinks and other facial movements typically range from 3-15 mA across the above-mentioned range of pulse widths. Greater stimulation may be needed in order to elicit complete blinks or the desired range of other facial movements in some individuals, but strong stimulation can be uncomfortable, and is not always tolerable. Accordingly, system 100 can be calibrated by adjusting the pulse train length, pulse amplitude, and/or pulse width for the stimulation sequence shown in FIG. 15 using controller 170 to elicit complete blinks or other facial movements for a particular user while minimizing the user's discomfort. In addition, electrodes 111-114 can be re-positioned to determine the most effective face surface stimulation locations for eliciting blinks and other facial movements. Further, in certain embodiments, system 100 can be calibrated according to the relationship between pulse train parameters and the extent of non-blink facial movements (e.g., eyebrow raising, eyes squeezing closed, and smile) to ensure that suitable pulse trains are delivered to electrodes 111-114 to stimulate these non-blink facial movements. To perform such calibrations, pulse trains can be varied, e.g., in steps of 0.5 mA in amplitude and steps of 0.2 ms in pulse width, e.g., in an iterative process, to identify an appropriate set of stimulation parameters.

Further aspects, methods, and systems for stimulating facial nerves that can be used with system 100 are disclosed, for example, in the following publications, the entire contents of each of which is incorporated herein by reference: Frigerio et al., "A Closed-Loop Stimulation System Supplemented with Motoneuron Dynamic Sensitivity Replicates Natural Eye Blinks," *Otolaryngol. Head Neck Surg.* 146: 230-234 (2012); Cogan, S. F., "Neural stimulation and recording electrodes," *Ann. Rev. Biomed. Eng.* 10: 175-309

(2008); and Frigerio, A. et al., "Surface Electromyography Recording of Spontaneous Eyeblinks: Applications in Neuroprosthetics," *Otolaryngol. Head Neck Surg.*, doi: 10.1177/0194599812469352 (2012).

Table 1 below summarizes the facial expressions that are detected on one side of the user's face by the embodiment of system 100 shown in FIG. 1, based on patterns of blocked and unblocked radiation paths between sources 1-4 and detectors 101-104, and also indicates which of the facial nerve branches are stimulated by system 100 to produce a similar response on the other side of the user's face.

TABLE 1

| Source/Detector Radiation Path (1 = unblocked, 0 = partially/fully blocked) | | | | | Stimulated Facial |
|---|---|---|---|---|---|
| 1-101 | 2-102 | 3-103 | 4-104 | Facial Expression | Nerve Branch |
| 0 | 1 | 1 | 1 | Forward Gaze | None |
| 0 | 1 | 1 | 1 | Lateral Gaze | None |
| 0 | 0 | 1 | 1 | Downward Gaze | None |
| 1 | 1 | 1 | 1 | Upward Gaze | Temporal* |
| 0 | 0 | 0 | 1 | Eye Blink | Zygomatic** |
| 0 | 0 | 0 | 0 | Eye Squeezed Closed | Zygomatic* |
| 0 | 1 | 0 | 0 | Smile | Zygomatic*,***, Buccal* |
| 1 | 1 | 1 | 1 | Eyebrow Raised | Temporal* |

*Pulse train persists for duration of desired facial expression.
**Pulse train is short (e.g., about 50 ms) to produce one blink.
***Pulse train is just strong enough to slightly narrow the user's palpebral fissure during smile without causing complete eye closure.

Figure 16:
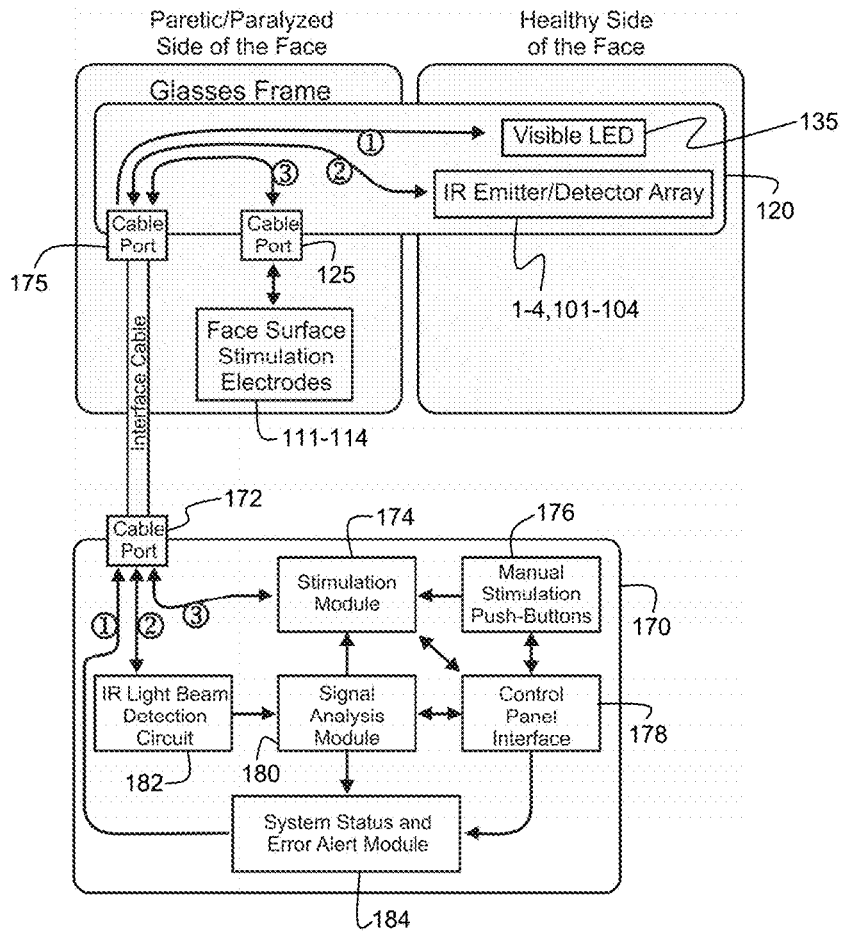
FIG. 16 is a schematic diagram of a controller for a facial movement detection system.

FIG. 16 shows a schematic diagram of controller 170. Controller 170 includes a port 172 to which an interface cable connects. The interface cable is also connected to port 175 so that controller 170 can transmit signals to, and receive signals from, radiation sources 1-4, detectors 101-104, and electrodes 111-114. Controller 170 includes a stimulation module 174 that determines suitable electrical signals for stimulating the user's facial nerves, a control panel interface 178 for activating system 100 and adjusting various system parameters, one or more optional manual stimulation buttons 176, a radiation detection circuit 182 and a signal analysis module 180 which together process signals generated by detectors 101-104, and a system status module 184 that generates system status and/or error messages using interface 178.

Controller 170 can also include an internal storage device for storing operating parameters. The operating parameters can include clinician-adjustable settings and user-adjustable settings. Clinician-adjustable settings, which can be determined at a clinic when the user is fitted with system 100, can be password protected to prevent user changes. User-adjustable settings can include stimulation pulse train amplitude (e.g., within a pre-determined range), and enabling and disabling of particular facial movement stimulations. Manual stimulation buttons 176, when activated by the user, allow the user to trigger any of the facial nerve stimulations that system 100 is configured to generate. For example, manual stimulation buttons 176 can include a control for stimulating an eye blink, and/or one or more proportional-control buttons for stimulating other facial movements. In some embodiments, the buttons can be configured so that stimulation of facial nerves persists for the duration of the button press. In certain embodiments, the pulse-train amplitude used to stimulate the user's facial nerves is proportional to how hard the buttons are pressed.

In some embodiments, system 100 includes an array of light emitting diodes (e.g., diode array 135 in FIG. 13) configured to provide various types of system information to the user. Although array 135 is positioned on an edge of support structure 120 in FIG. 13, more generally array 135 can be positioned at a variety of locations. For example, in some embodiments, array 135 is positioned directly in front of the eye around which sources 1-4 and detectors 101-104 are also positioned.

In general, array 135 is connected to controller 170 through support structure 120, and configured to illuminate so that it is visible only to the user under ordinary ambient light. Controller 170 transmits electrical signals to illuminate array 135 in a series of patterns to alert the user to a variety of information. A wide variety of alerting illumination patterns can be used. Non-limiting examples of such alerting events include the following.

The source-detector pairs are typically customized to the user's anatomy in a physician's clinic. Where support structure 120 is implemented as eyeglass frames, the medial set of radiation sources is mounted in such a way as to rest on the lateral surface of the nose between the nose pads of the eyeglass frames and the medial canthus of the eye. Although the medial surface of the set of radiation sources is form-fitting to the user's face, it may still need positional adjustment when the eyeglass frames are put on, and periodically during the day if/when the frames move position. Once an optimal position of the source-detector pairs has been achieved for a given individual during an initial fitting, the signal levels generated by each detector (during a forward gaze) are saved in the storage unit of controller 170 (e.g., a non-volatile computer memory) to represent an ideal system position.

Calibration Mode and Alert Functions

Each time the user puts on system 100 and activates it, the system can optionally enter a calibration mode. In the calibration mode, the signals generated by detectors 101-104 are compared to the stored (e.g., target) set of detector signals in controller 170. Controller 170 causes diode array 135 to blink rapidly if each of the radiation paths between sources 1-4 and detectors 101-104 are unblocked during a forward gaze (indicating that the source-detector pairs are too far from the surface of the user's face), to blink slowly if each of the radiation paths are blocked (indicating that the source-detector pairs are too close to the surface of the user's face), and to illuminate continuously when the detector signals sufficiently match the stored target signal values. In some embodiments, controller 170 automatically exits calibration mode after a selected time period (e.g., 2 seconds) during which system 100 is positioned on the user's face, and enters an active detection mode. In certain embodiments, controller 170 remains in calibration mode until the user issues a command (e.g., by activating a control on interface 178) to enter active detection mode. In general, the user can re-enter calibration mode at any time by activating another control on interface 178.

In some embodiments, controller 170 monitors electrode impedance (e.g., the resistance to electrical current passing between electrode 114 and each of electrodes 111-113), and alerts the user through a pattern of flashes of diode array 135 when high impedance is detected. High impedance can be caused, for example, by poor electrode contact with the skin. The pattern of flashes can further indicate which stimulation channel(s) is/are experiencing high impedance. A variety of different conditions can be applied by controller 170 to determine whether an electrode pair (e.g., electrode 114 and one of electrodes 111-113) has high impedance. In certain embodiments, an electrode pair is determined to have high impedance when the impedance exceeds a predetermined threshold (e.g., stored in the internal storage unit of controller 170). In some embodiments, an electrode pair is determined to have high impedance if the impedance for the electrode pair increases by a pre-determined percentage (e.g., stored in the internal storage unit of controller 170). In some embodiments, an electrode pair is determined to have high impedance if the impedance for the electrode pair increases from an initial impedance value at startup of system 100. In certain embodiments, an electrode pair is determined to have high impedance if the impedance for the electrode pair exceeds the impedance of the lowest-impedance electrode pair by a pre-determined percentage (e.g., stored in the internal storage unit of controller 170).

Similar criteria can also be used by controller 170 to determine whether the impedance for any of the electrode pairs is too low. If controller 170 determines that any electrode pair has an either an inappropriately high or low impedance, controller 170 alerts the user through a particular pattern of flashes of array 135 (e.g., a repeating pattern of two flashes separated by a 1 second pause to indicate abnormal impedance between the second pair of electrodes, 114 and 112). In certain embodiments, controller 170 can also disable stimulation of the user's facial nerves using the abnormal electrode pair until a suitable impedance value has been restored.

In general, system 100 operates under most outdoor and indoor lighting conditions, including complete darkness. However, in certain circumstances, a user's proximity to strong incandescent radiation sources or other sources of infrared radiation can affect the system's ability to successfully pair sources and detectors. When interfering sources of radiation are detected by controller 170, the controller alters the user by causing diode array 135 to pulse relatively slowly. In some embodiments, controller 170 can also disable facial nerve stimulation under these conditions until the interfering source(s) are no longer in proximity to the user.

As discussed above, controller 170 allows the user to change a variety of user-adjustable settings and operating parameters for system 100. In certain embodiments, when the user changes such settings and/or parameters, controller 170 causes diode array 135 to flash rapidly several times (e.g., 10 times) to confirm the change in settings, and to alert the user in the event that the settings were inadvertently changed.

In some embodiments, controller 170 includes a battery to provide electrical power to the various components of system 100. When the battery is drained below a predetermined capacity (e.g., 20%), controller 170 can cause diode array 135 to flash in an alternating pattern of short and long pulses that repeats at a regular interval (e.g., once every minute) to alert the user to the low battery condition. In certain embodiments, this low battery alert can be disabled by the user.

Hardware and Software

Methods for detecting facial movements and expressions of a user, and various functions of the systems described herein, can be performed by electronic processors (such as controller 170, which can include one or more processors and/or preprogrammed integrated circuits) executing programs based on standard programming techniques. Such programs are designed to execute on programmable computers or specifically designed integrated circuits, each comprising a processor, a data storage system (including memory and/or storage elements), at least one input device, and at least one output device, such as a display or printer. The program code is applied to input data to perform functions and generate output information, which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD-ROM or magnetic diskette) that, when read by a computer, can cause the processor to perform the analysis and control functions described herein.

Other Applications

In addition to detecting facial expressions and movements for stimulating the facial nerves of subjects afflicted with FNP, the systems and methods disclosed herein can also be used for a variety of other applications. In some embodiments, the systems and methods can be used to detect a user's facial movements for purposes of controlling a device. Facial movements such as eye blinks can be used, for example, to issue operating commands to devices such as a computer (e.g., to direct a pointing indicator on a computer screen). Facial movements can also be used to operate aspects of complex devices such as an aircraft, where activating all controls manually may prove too cumbersome and time consuming Facial movements can also be used to operate aspects of devices such as powered wheel chairs and other devices used by handicapped individuals, e.g., individuals who have one or more limbs paralyzed, but can blink or otherwise move portions of their face.

In certain embodiments, the systems and methods disclosed herein can be used to alert a user when he or she is falling asleep. For example, even very short periods of microsleep lasting a few tens or hundreds of milliseconds when a user is driving, flying (e.g., a pilot), or otherwise operating complex or heavy machinery (e.g., a crane operator) can be sufficient to cause a serious accident. The systems and methods disclosed herein can be incorporated into an alertness monitor which is configured to warn the user when the frequency or kinematics (e.g. rate and range) of blink or other facial movements indicate drowsiness by flashing a particular pattern through the diode array 135 or delivering particular electrical stimulation patterns to the face surface through the electrodes 111-114. Such alertness monitors can be worn by drivers, pilots, train operators, or others operating moving vehicles and devices, to warn such operators when their alertness is compromised. A threshold condition (e.g., one or more blinks lasting longer than a particular duration and/or when movements begin to slow beyond a particular threshold movement rate) can be used to determine whether a user warning should be issued.

In some embodiments, system 100 can be used to measure changes in reflexive or volitional facial movement frequency (e.g., how often the user's face moves) and/or kinematic properties of the user's facial movements (e.g., the rate and/or range of facial movements). As such properties are often related to the user's state of mind, system 100 can use such measurements to infer information about, e.g., the user's mood, state of well-being, and/or level of alertness, for a wide variety of purposes including (but not limited to) evaluating medication effectiveness and compliance, behavioral monitoring and modification, market research, and measuring teaching or training effectiveness. Likewise, system 100 can be used to detect changes in facial movements associated with a user's intent to volitionally control movements that are otherwise reflexive, and thereby detect when a user is undergoing stress and/or is speaking untruthfully.

EXAMPLE

The subject matter disclosed herein is further described in the following example, which is not intended to limit the scope of the claims.

To evaluate the methods disclosed herein for blink detection in a variety of different gaze positions (e.g., primary, lateral, upwards, and downwards) and facial expressions (e.g., broad smile, squinting, and eyebrow raising), video-recorded blinks were compared against measured results from a source-detector pair mounted to eyeglass frames.

An infrared LED and detector were mounted on three pairs of laboratory safety eyeglasses as a proof of concept, with each pair of glasses differing slightly in terms of the relative position of the infrared emitter/detector units in relation to the nose bridge to accommodate a range of different adult face shapes. The three pairs had beam positions that differed by less than 2 mm in relation to the lower rim and front surface of the glasses lens. The main difference among the glasses was that pair 2 had slightly narrower nose pad separation compared to the wider nose pads of pairs 1 and 3. Additionally, pair 3 had the beam falling slightly closer to the lens surface (1.3 mm closer than pair 1, and 1 mm closer than pair 2).

For each prototype pair of glasses, the infrared LED (QEC 123, obtained from Fairchild Semiconductor) had a peak emission wavelength of 880 nm, which was also the frequency of maximal sensitivity for the matching phototransistor (QSC 114, obtained from Fairchild Semiconductor). The LED and detector components were positioned at the nasal and temporal aspects of one eye (respectively), causing the infrared beam to pass horizontally across the central portion of the palpebral fissure, just anterior to the corneal surface.

The beam remained unbroken when the eye was open, but was interrupted by the eyelashes and/or lid tissue when the upper lid descended, causing the circuit receiving the infrared detector signal to drop in output voltage, as described herein. The LED was powered with electrical pulses at a frequency of 5.2 kHz, and the detector compared the light received during pulses versus infrared light detected between pulses to reject signal artifact due to changes in ambient light levels. An opaque light shield was mounted on the detector to reduce the potential impact of infrared light entering from glancing angles.

Infrared light emitted from the LED in each prototype pair of glasses did not pose a risk to the eye (e.g., lens, cornea, or retina). The maximal power output of the LEDs was 0.62 mW as measured at the LED lens surface using an infrared-sensitive light meter (Ophir Nova II Meter and Photodiode Power Sensor PD300, with appropriate filter setting).

Twenty-four volunteers aged 22-62 (10 males, 14 females; 20 Caucasians, 4 Asians, 1 African American) were recruited. Individuals with a history of eye/retinal disease, neuromuscular disease (myasthenia gravis, essential blepharospasm, or facial palsy), or pathological exophthalmos (i.e., Basedow-Graves disease) were excluded from participation. Seventeen individuals were under age 40, 6 were between 40 and 59 years old, and 1 was over 60 years old.

The study was performed in a distraction-free room. Participants were briefly tested/screened with the three prototype pairs of eyeglasses to determine which pair provided the best blink detection given their particular orbital anatomy. They were then asked to stand 50 cm from a Smart Board Screen (SBX880) with their chin resting on an adjustable platform which stabilized their head and oriented their forward gaze directly toward the screen. The testing session began with an instructional video projected in the center of the screen directly in front of the participant. The video was a close-up view of woman's face as she explained details of the testing session, including: (1) the total session length (6 minutes); (2) the need to keep the head steady and to move eyes only when instructed (rather than moving the head); (3) the task of visually tracking a large dot in various locations on the screen; and (4) the task of mimicking various facial expressions being modeled on the screen. Data collection began at the start of the introductory video in order to sample spontaneous blinking during forward gaze.

Data acquisition continued in the second part of the testing session, where participants were instructed to focus their gaze on a large dot appearing at various locations on the projection screen, without moving their head when changing their gaze position. The dot changed position every 5 seconds, with an audible tone indicating when the dot was changing position. The sequence of dot locations was repeated twice, and included the following sequence: Center, Center Up, Center Down, Center, Left, Left Up, Left Down, Center, Right, Right Up, Right Down, Center. This enabled testing of the effect of gaze direction on the blink detection circuit output, since upper eyelid position can potentially change based upon gaze change and position (particularly for downward gaze).

In the third part of the testing session, participants were shown photographs of four different facial expressions (neutral, smiling, squinting and eyebrows raising) and asked to mimic each expression throughout the 4 seconds each expression was shown. The neutral expression was mimicked first, and also fell between each of the other three expressions. Each time the demonstration expression changed, an audible narration accompanied the visual cue, informing participants of the desired facial expression.

Video and audio data were recorded using a video camera (Canon VIXIA HF R200, 1440×1080 pixels, 11,951 kbps video; 48 kHz, 256 kbps audio) positioned on a tripod with a close-up fronto-lateral view of each participant's eye being monitored, and an output voltage from the blink detection circuit and room microphone digitized at 20 kHz using analog-to-digital hardware (DigiData 1440 and a Cyberamp 380 programmable filter/amplifier, obtained from Molecular Devices, Sunnyvale, Calif.) and software (Clampex 10.2, obtained from Molecular Devices). Video files were viewed on a computer using software (Corel VideoStudio Pro X5) that allowed the viewer to indicate each point in time (e.g., each frame, at a frame rate of 29.97 fps) when a blink or eye twitch began. A blink was noted when the upper and lower edge of the pupil was at least partially covered by the eyelids, and a twitch was noted when there was a conspicuous movement of one or both lids without covering the upper and lower edge of the pupil. Each video was viewed a minimum of 2 times to ensure that all blinks were noted, and observers were blinded to the blink detection circuit output. The time locations for observed eyelid movements, gaze position changes, and mimicked facial expressions were compared with the absolute value and rate of change of the detection circuit output.

The rate of signal change, represented by the signal's derivative (i.e., instantaneous velocity), was calculated in MATLAB software using the "diff" function (MathWorks Inc., Natick, Mass.) after down sampling from 20 kHz to 1 kHz. Signals that started from ≥3V and had derivative values of either ≤−0.1 or ≤−0.2 were scored as blinks. Of these two levels, the particular derivative threshold applied for blink assessment was determined on an individual basis according to which level produced the least amount of detection error (i.e., fewest false positives and false negatives). Once a threshold level was selected for an individual, that level was applied for blink detection throughout their recording session. Signal changes that occurred less rapidly than the applied threshold or that occurred from a starting level<3 V were not scored as blinks, nor were signals that occurred within 250 ms of a detected blink (to avoid potential artifacts associated with eye opening at the end of each blink).

To qualitatively relate the detection circuit output (V) with change in palpebral fissure during blinking, the detection system was also employed for two participants (a male age 43 and a female age 32) in conjunction with high-speed video recording of eyelid movement (1000 frames/sec, 240× 256 pixels, using a KayPentax B/W System).

At least one of the three prototype pairs of eyeglasses fit each participant adequately for blink detection. The three different glasses versions (pairs 1-3) were worn by 50%, 37.5% and 12.5% of the participants, respectively, with fairly even numbers of males and females wearing the two most commonly worn versions (pairs 1 and 2). Pairs one and two differed primarily in the position of the nose bridge pads, causing pair 1 to rest slightly lower on the face than pair 2 due to differing gaps between nose bridge pads. Pair 3 had a beam falling 1.3 mm or 1 mm further from the eye surface than pairs 1 and 2, respectively, which provided the best blink detection during the initial testing/fitting in only 3 participants. In all four participants of Asian descent and two of the Caucasian participants, the lower rim of the glasses rested on the upper cheek (lower orbit and malar fat pad) rather than the bridge of the nose, and therefore moved with changes in facial expression, potentially decreasing blink detection accuracy. At no time did participants report seeing light or feeling heat from the infrared LED, consistent with the 880 nm peak wavelength and relatively low power output of the LED and driving circuit.

The airing of the instructional video provided an opportunity to measure spontaneous blinks from participants during a forward gaze. The 24 participants produced a range of 1-76 complete blinks (mean=27.3, standard deviation=17.7) during the 101 seconds of instructional video.

A relatively unbroken light path between the infrared emitter and detector caused a relatively high voltage output (typically 4-5 V) from the detection circuit. When the infrared light path was broken, the circuit output voltage dropped towards a low state (typically 0-1 V). Drops in the circuit voltage caused by eyelid obstruction of the infrared light path during blinking were generally faster than when light path obstruction occurred during gaze changes and facial expressions (i.e., squinting and broadly smiling). As a consequence, both the direction and magnitude of signal change and the rate of signal change were considered when identifying blinks from the detection circuit output.

Blink detection based on changes in signal magnitude achieved 100% sensitivity in forward gaze, but typically generated false detections on downward gaze and, to a lesser degree, other gaze changes as well. Blink detection based on peak rate of signal change (e.g., first derivative) during the instructional video where participants maintained a primary (forward) gaze yielded an average correct detection of 87%, with 11% false positives, and 2% false negatives. Of the 11% false positives, slightly over half (6%) were associated with eye twitches (i.e., partial eyelid closures). Therefore, the system had reasonably good sensitivity for blink detection during primary gaze (missing only 2% of observed blinks on average, and missing no blinks in 14 of 24 participants), but falsely detected blinks when no visible eyelid movement occurred for 5% of the detected blink events. For the 21 gaze changes (starting from a primary gaze) tested in each participant, the resulting blink detection signal pattern was falsely identified as a blink 6.3% of the time for lateral eye movements, 10.4% of the time for upward movements, 46.5% of the time for downward movements, and 5.6% of the time for movements from an upward or downward gaze back to the central (primary) gaze.

Blink detection was not attempted during the mimicked facial expressions, but a change in the signal baseline during these expressions would have often precluded blink detection due to interruption of the infrared light beam by the upper and/or lower eyelid. Interruption of the infrared light path during these expressions was typically associated with partial eyelid closure (i.e., during squinting or broad smile), but was also affected by shifting of the glasses by movement of skin at the bridge of the nose or upper cheek (i.e., during eyebrow raising and broad smiling). Specifically, the infrared circuit output was reduced to 2.5 V (half) or less during broad smiling in 57% of participants, during squinting in 96% in of participants, and during eyebrow raising in 22% of participants.

Comparison between the blink detection circuit output and high-speed-video (1000 fps) recordings of eyelid movement indicated that the initiation of signal change (deflection) from baseline was synchronous with visible eyelid movement. The average latency from the start of signal deflection during a blink to peak derivative was 45.6 ms (±18.9 ms). Thus, this example demonstrates that the present systems and methods can be used effectively as described herein.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:
1. A system for detecting a user's facial movement, facial expression, or both, the system comprising:
 a plurality of radiation sources;
 a plurality of radiation detectors, wherein each radiation detector is paired with a different one of the radiation sources and configured to detect radiation emitted by its paired radiation source; and
 a controller connected to the radiation detectors and configured to:
  receive signals corresponding to measurements of emitted radiation from each of the radiation detectors;
  determine, for each radiation source-detector pair, information about whether a radiation path between the source and detector is blocked by a different portion of the user's face; and
  determine a facial movement or facial expression or both of the user based on the information,
 wherein a first one of the radiation source-detector pairs comprises a radiation source and a detector adapted to be located on opposite sides of the user's eye to define a first radiation path adjacent to the user's supraorbital fat pad, and the controller is configured to determine information about whether the first radiation path is blocked by the user's supraorbital fat pad; and wherein a second one of the radiation source-detector pairs comprises a radiation source and a detector adapted to be located on opposite sides of the user's eye to define a second radiation path adjacent to the user's malar fat pad, and the controller is configured to determine information about whether the second radiation path is blocked by the user's malar fat pad.

2. The system of claim 1, wherein the plurality of radiation sources comprises at least three or four radiation sources.

3. The system of claim 1, further comprising a support structure, wherein the plurality of radiation sources and the plurality of radiation detectors are integrated into or attached to the support structure.

4. The system of claim 3, wherein the support structure comprises eyeglass frames.

5. The system of claim 3, wherein the plurality of radiation sources and the plurality of radiation detectors are connected to the controller through or by means of the support structure.

6. The system of claim 3, wherein the support structure comprises a member to which the plurality of radiation sources and the plurality of detectors are attached, and wherein the support structure is configured to be attached to eyeglass frames.

7. The system of claim 3, comprising a plurality of electrodes each connected to the controller and configured to transmit an electrical signal to a facial nerve of the user.

8. The system of claim 7, wherein the plurality of electrodes is attached to the support structure.

9. The system of claim 7, wherein the plurality of electrodes is connected to the controller through the support structure.

10. The system of claim 8, wherein the controller is configured to transmit electrical signals to the plurality of electrodes to apply the electrical signals to one or more facial nerves of the user.

11. The system of claim 1, wherein each of the plurality of radiation sources emits radiation having a different central wavelength.

12. The system of claim 1, wherein radiation emitted by each of the radiation sources has a modulation frequency and a modulation phase, and wherein the modulation phase of the emitted radiation is different for each of the radiation sources.

13. The system of claim 1, wherein each of the radiation detectors comprises a photodiode.

14. The system of claim 1, wherein the controller is further configured to determine the user's facial movement or expression based on a rate of change of detected emitted radiation from one or more of the plurality of radiation sources.

15. The system of claim 1, wherein the controller is configured to determine whether the user's facial movement or expression corresponds to one of at least eight different facial movements or expressions, and wherein the at least eight different facial movements or expressions comprise a forward gaze, a lateral gaze, a downward gaze, an upward gaze, an eye blink, a squeezed eye closure, a smile, and an eyebrow raised movement or expression.

16. A method for detecting a user's facial movement or expression, the method comprising:
positioning a plurality of pairs of radiation sources and radiation detectors adjacent to a user's face, wherein a first one of the source-detector pairs comprises a radiation source and a radiation detector positioned on opposite sides of the user's eye to define a first radiation path adjacent to the user's supraorbital fat pad, wherein a second one of the source-detector pairs comprises a radiation source and a radiation detector positioned on opposite sides of the user's eye to define a second radiation path adjacent to the user's malar fat pad, and wherein each additional source-detector pair forms an additional radiation path;
for the first source-detector pair, directing radiation along the first radiation path, and determining information about whether the first radiation path is blocked by the user's supraorbital fat pad;
for the second source-detector pair, detecting radiation along the second radiation path, and determining information about whether the second radiation path is blocked by the user's malar fat pad;
for each additional source-detector pair, directing radiation from the source toward the detector along the corresponding additional radiation path, and determining information about whether the additional radiation path is blocked by a different portion of the user's face; and
determining a facial movement or expression of the user based on the information.

17. The method of claim 16, wherein each of the radiation sources emits radiation having a different central wavelength.

18. The method of claim 16, comprising modulating the radiation emitted by each of the radiation sources according to a modulation frequency and a modulation phase, wherein the modulation phases of each of the radiation sources are different.

19. The method of claim 16, comprising transmitting signals corresponding to measurements of emitted radiation from the radiation detectors to a controller through a support structure, wherein the support structure comprises eyeglass frames.

20. The method of claim 16, comprising:
determining the user's facial movement or expression based on a rate of change of detected radiation emitted from one or more of the plurality of radiation sources; and
determining whether the user's facial movement or expression corresponds to one of at least eight different facial movements or expressions.

* * * * *

UNITED STATES PATENT AND TRADEMARK OFFICE
CERTIFICATE OF CORRECTION

PATENT NO. : 9,625,251 B2
APPLICATION NO. : 14/760944
DATED : April 18, 2017
INVENTOR(S) : James Tracey Heaton et al.

It is certified that error appears in the above-identified patent and that said Letters Patent is hereby corrected as shown below:

In the Claims

In Column 22, Line 11 (approx.), in Claim 16, delete "eve" and insert -- eye --

Signed and Sealed this
Third Day of October, 2017

Joseph Matal
*Performing the Functions and Duties of the*
*Under Secretary of Commerce for Intellectual Property and*
*Director of the United States Patent and Trademark Office*